US010876122B2

(12) United States Patent
Seo et al.

(10) Patent No.: US 10,876,122 B2
(45) Date of Patent: Dec. 29, 2020

(54) METHOD OF PRODUCING 2'-FUCOSYLLACTOSE USING RECOMBINANT *CORYNEBACTERIUM GLUTAMICUM*

(71) Applicants: SEOUL NATIONAL UNIVERSITY R&DB FOUNDATION, Seoul (KR); ADVANCED PROTEIN TECHNOLOGIES CORP., Suwon-si (KR)

(72) Inventors: Jin-Ho Seo, Seoul (KR); Young-Wook Chin, Seongnam-si (KR); Hae-Yong Jo, Seoul (KR)

(73) Assignees: SEOUL NATIONAL UNIVERSITY R&DB FOUNDATION, Seoul (KR); ADVANCED PROTEIN TECHNOLOGIES CORP., Suwon-si (KR)

( * ) Notice: Subject to any disclaimer, the term of this patent is extended or adjusted under 35 U.S.C. 154(b) by 0 days.

(21) Appl. No.: 16/589,724

(22) Filed: Oct. 1, 2019

(65) Prior Publication Data

US 2020/0048640 A1 Feb. 13, 2020

Related U.S. Application Data

(62) Division of application No. 15/574,028, filed as application No. PCT/KR2017/004340 on Apr. 24, 2017, now Pat. No. 10,570,399.

(30) Foreign Application Priority Data

Apr. 25, 2016 (KR) ........................ 10-2016-0050219

(51) Int. Cl.

| | |
|---|---|
| ***C12N 15/52*** | (2006.01) |
| ***C12P 19/00*** | (2006.01) |
| ***C12N 9/88*** | (2006.01) |
| ***C12N 9/10*** | (2006.01) |
| ***C12N 9/04*** | (2006.01) |
| ***C07K 14/34*** | (2006.01) |
| ***C12N 15/77*** | (2006.01) |
| ***C12P 19/04*** | (2006.01) |

(52) U.S. Cl.

CPC .............. *C12N 15/52* (2013.01); *C07K 14/34* (2013.01); *C12N 9/0006* (2013.01); *C12N 9/1051* (2013.01); *C12N 9/88* (2013.01); *C12N 15/77* (2013.01); *C12P 19/00* (2013.01); *C12P 19/04* (2013.01); *C12Y 101/01271* (2013.01); *C12Y 402/01047* (2013.01)

(58) Field of Classification Search

None

See application file for complete search history.

(56) References Cited

U.S. PATENT DOCUMENTS

| | | | | |
|---|---|---|---|---|
| 6,875,591 | B1 * | 4/2005 | Koizumi ................ | C12P 19/32 435/105 |
| 9,944,965 | B2 * | 4/2018 | Lee ........................ | C12P 19/18 |
| 10,336,990 | B2 * | 7/2019 | Kim ....................... | C12P 19/00 |
| 2004/0058418 | A1 | 3/2004 | Endo et al. | |

FOREIGN PATENT DOCUMENTS

| | | | |
|---|---|---|---|
| CN | 103562401 | A | 2/2014 |
| CN | 103667371 | A | 3/2014 |
| CN | 104531597 | A | 4/2015 |
| CN | 104780785 | A | 7/2015 |
| JP | 2014-506474 | A | 3/2014 |
| KR | 20020062361 | A | 7/2002 |
| KR | 20120022875 | A | 3/2012 |
| KR | 20120122098 | A | 11/2012 |
| KR | 20140046414 | A | 4/2014 |
| KR | 101544184 | B1 | 8/2015 |
| KR | 101648352 | B1 | 8/2016 |
| WO | 01/46400 | A1 | 6/2001 |
| WO | 2015/150328 | A1 | 10/2015 |
| WO | WO2015150328 | * | 10/2015 |

OTHER PUBLICATIONS

Chica et al. Curr Opin Biotechnol. Aug. 2005;16(4):378-84. (Year: 2005).*

Singh et al. Curr Protein Pept Sci. 2017, 18, 1-11 (Year: 2017).*

Chin et al. J Biotechnol. Sep. 20, 2015;210:107-15. Epub Jul. 17, 2015. (Year: 2015).*

Young-Wook Chin et al., Metabolic engineering of Corynebacterium glutamicum to produce GDP-L-fucose from glucose and mannose, Bioprocess Biosyst Eng (2013) 36:749-756.

Young-Wook Chin et al., Enhanced production of 2'-fucosyllactose in engineered *Escherichia coli* BL21star(DE3) by modulation of lactose metabolism and fucosyltransferase, Elsevier B.V., Journal of Biotechnology 210 (2015) 107-115.

(Continued)

*Primary Examiner* — Christian L Fronda

(74) *Attorney, Agent, or Firm* — Sughrue Mion, PLLC

(57) ABSTRACT

Provided is a method of producing 2'-fucosyllactose including culturing in a medium supplemented with lactose a recombinant *Corynebacterium glutamicum* transformed to express α-1,2-fucosyltransferase, transformed to express GDP-D-mannose-4,6-dehydratase, transformed to express GDP-L-fucose synthase, and transformed to express lactose permease, wherein the recombinant *Corynebacterium glutamicum* has phosphomannomutase and GTP-mannose-1-phosphate guanylyltransferase.

4 Claims, 7 Drawing Sheets

Specification includes a Sequence Listing.

(56) References Cited

OTHER PUBLICATIONS

Accession BCD97538. Dec. 3, 2015. (Year: 2015).
Accession BX927150. Feb. 27, 2015 (Year: 2015).
Accession AQY87614. Jul. 10, 2008 (Year: 2008).
Accession BCD97562. Dec. 3, 2015 (Year: 2015).
Florian Baumgärtner et al; "Construction of *Escherichia coli* strains with chromosomally integrated expression cassettes for the synthesis of 2'-fucosyllactose"; Micorbial Cell Factories; vol. 12; No. 40; 2013; pp. 1-13 (total 13 pages).
Barbara Petschacer et al; "Biotechnological production of fucosylated human milk oligosaccharides: Prokaryotic fucosyltransferases and their use in biocatalytic cascades or whole cell conversion systems"; Journal of Biotechnology; vol. 235; 2016; pp. 61-83 (total 23 pages).

* cited by examiner

Identity positions : 82.9%

SEQUENCE LISTING

<160> NUMBER OF SEQ ID NOS: 6

<210> SEQ ID NO 1
<211> LENGTH: 1377
<212> TYPE: DNA
<213> ORGANISM: Corynebacterium glutamicum ATCC 13032

<400> SEQUENCE: 1
atgcgtaccc gtgaatctgt cacggctgta attaaggcgt atgacgtccg tggtgttgtt 60
ggtgtcgata ttgatgctga tttcatttct gagactggcg ctgcctttgg tcggctcatg 120
cgtagtgagg gtgaaaccac cgttgctatt ggccatgaca tgcgtgattc ctcccctgaa 180
ttggccaagg cgtttgccga tggcgtgact gcacagggtt tggatgttgt tcatttggga 240
ctgacttcta ctgatgagct gtactttgcg tccggaacct tgaagtgtgc tggtgcgatg 300
tttactgcgt cgcataaccc cgctgagtac aacggcatca agttgtgtcg tgcgggtgct 360
cgtccggtcg gtcaggattc tggtttggcc aacatcattg atgatctggt tgagggtgtt 420
ccagcgtttg atggtgagtc aggttcggtt tctgagcagg atttgctgag cgcatatgcc 480
gagtacctca atgagcttgt tgatctgaag aacatccgcc cgttgaaggt tgctgtggat 540
gcggcaaacg gcatgggtgg gttcactgtc cctgaggtat tcaagggtct gccacttgat 600
gttgcgccac tgtattttga gcttgacggc aatttcccca accatgaggc caatcctctg 660
gagcctgcca acctggttga tttgcagaag tttaccgtag agaccggatc tgatatcggt 720
ttggcgttcg acggcgatgc ggatcgttgc ttcgtggtcg atgagaaggg ccagccagtc 780
agcccttcgg cgatctgtgc gatcgtagcg gagcgttact tggagaagct tccgggttcc 840
accatcatcc acaacctgat tacctctaag gctgtgcctg aggtgattgc tgaaaacggt 900
ggcactgcgg tgcgtactcg cgtgggtcac tccttcatca aggcgaagat ggcagagacc 960
ggtgcggcct ttggtggcga gcactctgcg cactactact tcactgagtt cttcaatgcg 1020
gactccggca ttttggctgc gatgcacgtg ctggctgcgc tgggaagcca ggaccagcca 1080

```
ctcagtgaga tgatggctag gtataaccgg tacgttgctt caggcgagtt gaactcccgt   1140

ttggctaatg cagaggcgca gcaagagcgc acccaggctg tgctcgatgc gttcgctgat   1200

cgcaccgagt ccgtggacac ccttgacggc gtgactgtgg aactcaagga cacctccgcg   1260

tggttcaacg tgcgtgcgtc caacaccgag ccgctgcttc gcctcaatgt tgaagctgca   1320

tcgaaggaag aagtcgatgc gttggtagcg gagattctag ggattatccg cgcataa      1377


<210> SEQ ID NO 2
<211> LENGTH: 1089
<212> TYPE: DNA
<213> ORGANISM: Corynebacterium glutamicum ATCC 13032

<400> SEQUENCE: 2

atgactttaa ctgacaacag caaaaacgtt gatgctgtca tcttggtcgg tggcaaaggt     60

acccgactgc gcccccctgac cgtcaatact ccaaagccaa tgctgccaac tgctggccac    120

ccattcttga cccacctttt ggcccgcatc aaggccgcag gcatcacaca cgtcgtgctg    180

ggaacgtcat tcaaagctga agtcttcgag gaatacttcg gagatggctc cgaaatgggc    240

ttggaaattg aatatgtcgt cgaggatcag cctttgggca ctggtggtgg catccgaaac    300

gtctacgaca agctgcgtca cgatactgcg attgtgttca acggcgatgt gctctccggt    360

gcggatctca acagcattct ggacacccac cgcgaaaagg acgcagatct gaccatgcat    420

ctcgtgcgcg tagctaaccc tcgtgcgttt ggttgcgtcc ccaccgatga ggatggtcgc    480

gtcagcgaat tccttgaaaa gaccgaagat ccaccaaccg atcagatcaa cgccggctgc    540

tacgtgttca agaaggaact catcgagcag atcccggcag gccgagcagt ttccgtcgag    600

cgcgaaacct tccctcagct gttggaagaa ggcaagcgag tcttcggcca cgtcgacgct    660

tcctactggc gcgacatggg caccccaagc gacttcgtcc gcggctcggc tgacctggtc    720

cgcggcattg cgtactcccc attgctcgaa ggcaaaacag gagagtcgct tgtcgacgcc    780

tccgccggcg ttcgcgacgg cgtcctgctg ctcggcggaa ccgtagtcgg ccgcggcact    840

gagatcggtg ccggctgccg cgttgacaac actgttattt tcgacggcgt caccattgaa    900

ccaggtgcgg tcattgaaaa ttccatcatt tcctcgggag cacgcatcgg tgctaatgcg    960

cacatctccg gttgcatcat tggcgagggc gcacaggttg gtgctcggtg tgaactcaac   1020

gcagggatgc gcgtcttccc aggcgttgtg atcccagaca gcggaattcg tttttcgtct   1080

gatcagtag                                                           1089


<210> SEQ ID NO 3
<211> LENGTH: 2090
<212> TYPE: DNA
<213> ORGANISM: E.coli K-12 MG1655

<400> SEQUENCE: 3

atgtcaaaag tcgctctcat caccggtgta accggacaag acggttctta cctggcagag     60

tttctgctgg aaaaaggtta cgaggtgcat ggtattaagc gtcgcgcatc gtcattcaac    120

accgagcgcg tggatcacat ttatcaggat ccgcacacct gcaacccgaa attccatctg    180

cattatggcg acctgagtga tacctctaac ctgacgcgca ttttgcgtga agtacagccg    240

gatgaagtgt acaacctggg cgcaatgagc cacgttgcgg tctcttttga gtcaccagaa    300

tataccgctg acgtcgacgc gatgggtacg ctgcgcctgc tggaggcgat ccgcttcctc    360

ggtctggaaa agaaaactcg tttctatcag gcttccacct ctgaactgta tggtctggtg    420
```

-continued caggaaattc cgcagaaaga gaccacgccg ttctacccgc gatctccgta tgcggtcgcc 480
aaactgtacg cctactggat caccgttaac taccgtgaat cctacggcat gtacgcctgt 540
aacggaattc tcttcaacca tgaatccccg cgccgcggcg aaaccttcgt tacccgcaaa 600
atcacccgcg caatcgccaa catcgcccag ggctggagt cgtgcctgta cctcggcaat 660
atggattccc tgcgtgactg ggccacgcc aaagactacg taaaaatgca gtggatgatg 720
ctgcagcagg aacagccgga agatttcgtt atcgcgaccg gcgttcagta ctccgtgcgt 780
cagttcgtgg aaatggcggc agcacagctg ggcatcaaac tgcgctttga aggcacgggc 840
gttgaagaga agggcattgt ggtttccgtc accgggcatg acgcgccggg cgttaaaccg 900
ggtgatgtga ttatcgctgt tgacccgcgt tacttccgtc cggctgaagt tgaaacgctg 960
ctcggcgacc cgaccaaagc gcacgaaaaa ctgggctgga aaccggaaat caccctcaga 1020
gagatggtgt ctgaaatggt ggctaatgac ctcgaagcgg cgaaaaaaca ctctctgctg 1080
aaatctcacg gctacgacgt ggcgatcgcg ctggagtcat aagcatgagt aaacaacgag 1140
tttttattgc tggtcatcgc gggatggtcg gttccgccat caggcggcag ctcgaacagc 1200
gcggtgatgt ggaactggta ttacgcaccc gcgacgagct gaacctgctg gacagccgcg 1260
ccgtgcatga tttctttgcc agcgaacgta ttgaccaggt ctatctggcg gcggcgaaag 1320
tgggcggcat tgttgccaac aacacctatc cggcggattt catctaccag aacatgatga 1380
ttgagagcaa catcattcac gccgcgcatc agaacgacgt gaacaaactg ctgtttctcg 1440
gatcgtcctg catctacccg aaactggcaa aacagccgat ggcagaaagc gagttgttgc 1500
agggcacgct ggagccgact aacgagcctt atgctattgc caaaatcgcc gggatcaaac 1560
tgtgcgaatc atacaaccgc cagtacggac gcgattaccg ctcagtcatg ccgaccaacc 1620
tgtacgggcc acacgacaac ttccacccga gtaattcgca tgtgatccca gcattgctgc 1680
gtcgcttcca cgaggcgacg gcacagaatg cgccggacgt ggtggtatgg ggcagcggta 1740
caccgatgcg cgaatttctg cacgtcgatg atatggcggc ggcgagcatt catgtcatgg 1800
agctggcgca tgaagtctgg ctggagaaca cccagccgat gttgtcgcac attaacgtcg 1860
gcacgggcgt tgactgcact atccgcgagc tggcgcaaac catcgccaaa gtggtgggtt 1920
acaaaggccg ggtggttttt gatgccagca aaccggatgg cacgccgcgc aaactgctgg 1980
atgtgacgcg cctgcatcag cttggctggt atcacgaaat ctcactggaa gcggggcttg 2040
ccagcactta ccagtggttc cttgagaatc aagaccgctt tcgggggtaa 2090

<210> SEQ ID NO 4
<211> LENGTH: 916
<212> TYPE: DNA
<213> ORGANISM: helicobacter pylori ATCC 700392

<400> SEQUENCE: 4
aaggagatat acaatggctt ttaaggtggt gcaaatttgc ggagggcttg ggaatcaaat 60
gtttcaatac gctttcgcta aaagtttgca aaaacactct aatacgcctg tgctgttaga 120
tatcacttct tttgattgga gcgataggaa aatgcaatta gaacttttcc ctattgattt 180
gccctatgcg agcgcgaaag aaatcgctat agctaaaatg caacacctcc ccaagctagt 240
aagagacgcg ctcaaatgca tgggatttga tagggtgagt caagaaatcg tttttgaata 300
cgagcctaaa ttgctaaagc caagccgctt gacttatttt tttggctatt tccaagatcc 360
acgatacttt gatgctatat cccctttaat caagcaaacc ttcactctac cccccccccc 420
cgaaaataat aagaataata ataaaaaaga ggaagaatat cagtgcaagc tttctttgat 480

```
tttagccgct aaaaacagcg tgtttgtgca tataagaaga ggggattatg tggggattgg    540

ctgtcagctt ggtattgact atcaaaaaaa ggcgcttgag tatatggcaa agcgcgtgcc    600

aaacatggag ctttttgtgt tttgcgaaga cttagaattc acgcaaaatc ttgatcttgg    660

ctacccttttt atggacatga ccactaggga taaagaagaa gaggcgtatt gggacatgct    720

gctcatgcaa tcttgtcagc atgccattat cgctaatagc acttatagct ggtgggcggc    780

ctatttgata gaaaatccag aaaaaatcat tattggcccc aaacactggc tttttgggca    840

tgagaatatc ctttgtaagg agtgggtgaa aatagaatcc cattttgagg taaaatccca    900

aaagtataac gcttaa                                                     916
```

```
<210> SEQ ID NO 5
<211> LENGTH: 3335
<212> TYPE: DNA
<213> ORGANISM: E.coli

<400> SEQUENCE: 5

accatcgaat ggcgcaaaac ctttcgcggt atggcatgat agcgcccgga agagagtcaa     60

ttcagggtgg tgaatgtgaa accagtaacg ttatacgatg tcgcagagta tgccggtgtc    120

tcttatcaga ccgtttcccg cgtggtgaac caggccagcc acgtttctgc gaaaacgcgg    180

gaaaaagtgg aagcggcgat ggcggagctg aattacattc ccaaccgcgt ggcacaacaa    240

ctggcgggca aacagtcgtt gctgattggc gttgccacct ccagtctggc cctgcacgcg    300

ccgtcgcaaa ttgtcgcggc gattaaatct cgcgccgatc aactgggtgc cagcgtggtg    360

gtgtcgatgg tagaacgaag cggcgtcgaa gcctgtaaag cggcggtgca caatcttctc    420

gcgcaacgcg tcagtgggct gatcattaac tatccgctgg atgaccagga tgccattgct    480

gtggaagctg cctgcactaa tgttccggcg ttatttcttg atgtctctga ccagacaccc    540

atcaacagta ttattttctc ccatgaagac ggtacgcgac tgggcgtgga gcatctggtc    600

gcattgggtc accagcaaat cgcgctgtta gcgggcccat taagttctgt ctcggcgcgt    660

ctgcgtctgg ctggctggca taaatatctc actcgcaatc aaattcagcc gatagcggaa    720

cgggaaggcg actggagtgc catgtccggt tttcaacaaa ccatgcaaat gctgaatgag    780

ggcatcgttc ccactgcgat gctggttgcc aacgatcaga tggcgctggg cgcaatgcgc    840

gccattaccg agtccgggct gcgcgttggt gcggatatct cggtagtggg atacgacgat    900

accgaagaca gctcatgtta tatcccgccg ttaaccacca tcaaacagga ttttcgcctg    960

ctggggcaaa ccagcgtgga ccgcttgctg caactctctc agggccaggc ggtgaagggc   1020

aatcagctgt tgcccgtctc actggtgaaa agaaaaacca ccctggcgcc caatacgcaa   1080

accgcctctc cccgcgcgtt ggccgattca ttaatgcagc tggcacgaca ggtttcccga   1140

ctggaaagcg ggcagtgagc gcaacgcaat taatgtgagt tagctcactc attaggcacc   1200

ccaggcttta cactttatgc ttccggctcg tatgttgtgt ggaattgtga gcggataaca   1260

atttcacaca ggaaacagct atgtactatt taaaaaacac aaacttttgg atgttcggtt   1320

tattcttttt cttttacttt tttatcatgg gagcctactt cccgtttttc ccgatttggc   1380

tacatgacat caaccatatc agcaaaagtg atacgggtat tatttttgcc gctatttctc   1440

tgttctcgct attattccaa ccgctgtttg gtctgctttc tgacaaactc gggctgcgca   1500

aatacctgct gtggattatt accggcatgt tagtgatgtt tgcgccgttc tttattttta   1560

tcttcgggcc actgttacaa tacaacattt tagtaggatc gattgttggt ggtatttatc   1620
```

-continued taggcttttg ttttaacgcc ggtgcgccag cagtagaggc atttattgag aaagtcagcc 1680
gtcgcagtaa tttcgaattt ggtcgcgcgc ggatgtttgg ctgtgttggc tgggcgctgt 1740
gtgcctcgat tgtcggcatc atgttcacca tcaataatca gtttgttttc tggctgggct 1800
ctggctgtgc actcatcctc gccgttttac tctttttcgc caaaacggat gcgccctctt 1860
ctgccacggt tgccaatgcg gtaggtgcca accattcggc atttagcctt aagctggcac 1920
tggaactgtt cagacagcca aaactgtggt ttttgtcact gtatgttatt ggcgtttcct 1980
gcacctacga tgtttttgac caacagtttg ctaatttctt tacttcgttc tttgctaccg 2040
gtgaacaggg tacgcgggta tttggctacg taacgacaat gggcgaatta cttaacgcct 2100
cgattatgtt ctttgcgcca ctgatcatta atcgcatcgg tgggaaaaac gccctgctgc 2160
tggctggcac tattatgtct gtacgtatta ttggctcatc gttcgccacc tcagcgctgg 2220
aagtggttat tctgaaaacg ctgcatatgt ttgaagtacc gttcctgctg gtgggctgct 2280
ttaaatatat taccagccag tttgaagtgc gtttttcagc gacgatttat ctggtctgtt 2340
tctgcttctt taagcaactg gcgatgattt ttatgtctgt actggcgggc aatatgtatg 2400
aaagcatcgg tttccagggc gcttatctgg tgctgggtct ggtggcgctg ggcttcacct 2460
taatttccgt gttcacgctt agcggccccg gcccgctttc cctgctgcgt cgtcaggtga 2520
atgaagtcgc ttaagcaatc aatgtcggat gcggcgcgag cgccttatcc gaccaacata 2580
tcataacgga gtgatcgcat tgaacatgcc aatgaccgaa agaataagag caggcaagct 2640
atttaccgat atgtgcgaag gcttaccgga aaaaagactt cgtgggaaaa cgttaatgta 2700
tgagtttaat cactcgcatc catcagaagt tgaaaaaaga gaaagcctga ttaaagaaat 2760
gtttgccacg gtaggggaaa acgcctgggt agaaccgcct gtctatttct cttacggttc 2820
caacatccat ataggccgca atttttatgc aaatttcaat ttaaccattg tcgatgacta 2880
cacggtaaca atcggtgata acgtactgat tgcacccaac gttactcttt ccgttacggg 2940
acaccctgta caccatgaat tgagaaaaaa cggcgagatg tactcttttc cgataacgat 3000
tggcaataac gtctggatcg gaagtcatgt ggttattaat ccaggcgtca ccatcgggga 3060
taattctgtt attggcgcgg gtagtatcgt cacaaaagac attccaccaa acgtcgtggc 3120
ggctggcgtt ccttgtcggg ttattcgcga aataaacgac cgggataagc actattattt 3180
caaagattat aaagttgaat cgtcagttta aattataaaa attgcctgat acgctgcgct 3240
tatcaggcct acaagttcag cgatctacat tagccgcatc cggcatgaac aaagcgcagg 3300
aacaagcgtc gcatcatgcc tctttgaccc acagc 3335

<210> SEQ ID NO 6
<211> LENGTH: 903
<212> TYPE: DNA
<213> ORGANISM: Artificial Sequence
<220> FEATURE:
<223> OTHER INFORMATION: synthetic

<400> SEQUENCE: 6
atggcgttta aagtggtgca aatttgcgga ggcttgggta accaaatgtt tcagtacgcc 60
ttcgctaaaa gtttgcaaaa gcattccaac acgccggtgc tgctcgatat cactagcttt 120
gattggtctg atcgcaaaat gcaactggaa ctttttccga ttgacttgcc atacgcctcg 180
gcgaaagaga tcgcgatcgc taaaatgcag cacctcccga agctagtccg cgatgcactg 240
aagtgcatgg gcttcgaccg cgtgtctcaa gaaatcgttt tcgaatacga gccgaagctt 300
ctcaagccaa gccgcctcac ttatttcttc ggctacttcc aggacccacg atactttgat 360

-continued

```
gctatctccc ctttaatcaa gcaaaccttc accctgccac ccccccccga aaacaacaag    420

aataataata agaaagagga agagtatcag tgcaagcttt cactcatcct cgccgctaag    480

aatagcgtgt ttgttcacat ccgtcgcggt gactatgtcg gcattggctg tcagctgggt    540

attgattacc agaagaaggc tcttgagtac atggcaaagc gcgtgccaaa catggaactt    600

ttcgtgtttt gcgaagatct ggaattcaca cagaaccttg accttggata ccctttcatg    660

gatatgacca cccgtgacaa ggaggaagaa gcgtactggg acatgctgct catgcagtct    720

tgccagcacg ccattatcgc aaactccacc tattcgtggt gggcagcgta cttgatcgag    780

aacccagaaa agattattat tggccctaaa cactggttgt tcgggcacga aaacatcctg    840

tgtaaagagt gggtgaaaat cgaatcccat ttcgaggtca aatcccagaa gtataacgca    900

taa                                                                  903
```

METHOD OF PRODUCING 2'-FUCOSYLLACTOSE USING RECOMBINANT *CORYNEBACTERIUM GLUTAMICUM*

SEQUENCE LISTING

The Sequence Listing submitted in text format (.txt) filed on Oct. 1, 2019, named "SequenceListing.txt", created on Oct. 1, 2019, 12.9 KB, is incorporated herein by reference.

TECHNICAL FIELD

The present invention relates to recombinant *Corynebacterium glutamicum* (*C. glutamicum*) which is transformed to express α-1,2-fucosyltransferase, GDP-D-mannose-4,6-dehydratase (Gmd), GDP-L-fucose synthase (GDP-4-keto-6-deoxymannose-3,5-epimerase-4-reductase, WcaG) and lactose permease (LacY), and to overexpress phosphomannomutase (ManB) and GTP-mannose-1-phosphate guanylyltransferase (ManC), and a method for producing fucosyllactose using the same.

BACKGROUND ART

Human breast milk contains 200 or more kinds of human milk oligosaccharides (HMOs) having a unique structure at a considerably higher concentration (5 to 15 g/L) than other mammal's breast milk.

Breastfeeding during infancy is considerably important since HMOs provide various biological activities that have positive influences on infant development and health, such as prebiotic effects, prevention of pathogen infection, regulation of the immune system, and brain development.

Breast milk contains about 200 kinds of oligosaccharides. Among them, 2'-fucosyllactose and 3'-fucosyllactose are reported to be main HMOs that are involved in various biological activities. For this reason, in recent years, fucosyllactose draws a great deal of attention because it has potential to be used for powdered milks for infants, health functional food materials for elderly people and medicinal materials. However, it is known that about 20% of women cannot synthesize fucosyllactose well due to mutation of fucose transferase that synthesizes fucosyloligosaccharide. For this reason, there is a need for industrial production of fucosyllactose.

However, since industrial mass-production of fucosyllactose is difficult at present, instead of fucosyllactose, galactooligosaccharide or fructooligosaccharide, which is an analogue of fucosyllactose, is added to baby food, to offer similar effects thereto.

Meanwhile, methods of producing fucosyllactose include direct extrusion from breast milk, and chemical or enzymatic synthesis.

Direct extraction has drawbacks of limited breast milk supply and low productivity. Chemical synthesis has drawbacks of expensive substrates, low stereo-selectivity and production yield, and use of toxic organic solvents. In addition, enzymatic synthesis has drawbacks in that GDP-L-fucose used as a donor of fucose is very expensive and purification of fucosyltransferase involves high costs.

Due to the aforementioned drawbacks, it is difficult to apply direct extraction, and chemical or enzymatic production to mass-production of fucosyllactose and there are almost no technologies for mass-production. However, since it is possible to expect development of functional health foods and medicinal materials using 2'-fucosyllactose, a great deal of research is needed for industrial production of 2'-fucosyllactose using microorganisms.

In addition, the majority of conventional methods for producing 2'-fucosyllactose using microorganisms were production using recombinant *Escherichia coli*. However, most *Escherichia coli* used for experimentation are predominantly known to be harmful to customers although they are not pathogens.

In addition, since an ingredient for the cell membrane of *Escherichia coli* may serve as endotoxin, high isolation and purification costs are involved in the production of 2'-fucosyllactose. Accordingly, there is a difficulty in using *Escherichia coli* as a host cell that produces fucosyllactose which is one of food and medicinal materials.

DISCLOSURE

Technical Problem

Therefore, the present invention has been made in view of the above problems, and it is one object of the present invention to develop and provide a method for producing 2'-fucosyllactose at a high concentration, a high yield and a high productivity while using, as a host cell that produces fucosyllactose which is a food and/or medicinal material, *Corynebacterium glutamicum* that is safer than *Escherichia coli.*

Technical Solution

In accordance with the present invention, the above and other objects can be accomplished by the provision of recombinant *Corynebacterium glutamicum* which is transformed to express α-1,2-fucosyltransferase, is transformed to express GDP-D-mannose-4,6-dehydratase, is transformed to express GDP-L-fucose synthase, and is transformed to express lactose permease, wherein the recombinant *Corynebacterium glutamicum* has phosphomannomutase and GTP-mannose-1-phosphate guanylyltransferase.

The prevent inventors obtained a patent regarding a method for producing 2'-fucosyllactose using *Escherichia coli*, as Korean Patent No. 10-1544184 (2015.08.21). However, it has been frequently indicated that producing 2'-fucosyllactose for functional food additive applications using *Escherichia coli* may cause problems due to various safety-associated risks associated with *Escherichia coli*. Accordingly, in accordance with the present invention, there is an attempt to produce 2'-fucosyllactose using an alternative strain free of food safety problems.

The present invention adopts *Corynebacterium glutamicum* as a host cell producing 2'-fucosyllactose. Unlike conventionally used *Escherichia coli*, this strain is considered to be a GRAS (generally recognized as safe) strain which does not produce endotoxins and is widely used for industrially producing amino acids and nucleic acids that are food additives. Accordingly, *Corynebacterium glutamicum* is considered to be a stain suitable for production of food and medicinal materials and to advantageously eliminate customer fears about safety.

However, since *Escherichia coli* and *Corynebacterium glutamicum* have inherently different strain genetic properties, strategies different from *Escherichia coli* should be applied to *Corynebacterium glutamicum. Escherichia coli* and *Corynebacterium glutamicum* are the same in that external α-1,2-fucosyltransferase should be basically incorporated in order to produce 2'-fucosyllactose. However, *Corynebacterium glutamicum* further requires incorporation of GDP-D-mannose-4,6-dehydratase (Gmd), GDP-L-fucose synthase (this enzyme is called "GDP-4-keto-6-deoxy-D-mannose-3,5-epimerase-4-reductase" and is also simply referred to as "WcaG", and a gene encoding this enzyme is particularly referred to as "WcaG"), and lactose permease (LacY). That is, *Escherichia coli* has genes encoding GDP-D-mannose-4,6-dehydratase (Gmd), GDP-L-fucose synthase (WcaG), and lactose permease (LacY), but the *Corynebacterium glutamicum* strain has no genes encoding these enzymes, so incorporating such genes from an external source and expressing the same are needed.

In this case, the genes encoding α-1,2-fucosyltransferase are preferably derived from *Helicobacter pylori*, and genes encoding GDP-D-mannose-4,6-dehydratase (Gmd), GDP-L-fucose synthase (WcaG) and lactose permease (LacY) are preferably derived from *Escherichia coli.*

Meanwhile, the recombinant *Corynebacterium glutamicum* of the present invention is preferably transformed to overexpress phosphomannomutase, and overexpress GTP-mannose-1-phosphate guanylyltransferase. *Corynebacterium glutamicum* possesses genes encoding phosphomannomutase (ManB) and GTP-mannose-1-phosphate guanylyltransferase (ManC), and can thus express the same. Therefore, there may be no need to incorporate genes encoding the enzymes, but the enzymes should be overexpressed for mass-production. For this reason, the present invention requires transformation of *Corynebacterium glutamicum* in order to overexpress the two enzymes.

Meanwhile, the actions of the enzymes can be seen from FIG. 1 and a detailed explanation thereof is thus omitted. It should be noted that lactose permease (LacY) is an enzyme involved in transporting lactose present outside the strain to the inside thereof. In the following example of the present invention, lacYA genes lacZ of which is removed from Lac operon in *Escherichia coli* are incorporated for experimentation. However, since incorporating Lac operon in the present invention aims at incorporating lactose, there is no need to incorporate lacA genes and incorporation of only lacY genes is enough.

Meanwhile, the term "expression" as used herein means incorporation and expression of external genes into strains in order to intentionally express enzymes that cannot be inherently expressed by the *Corynebacterium glutamicum* strain according to the present invention, and the term "overexpression" as used herein means overexpression that is induced by artificially increasing the amount of expressed enzyme in order to increase expression for mass-production, although the *Corynebacterium glutamicum* strain according to the present invention has genes encoding the corresponding enzyme and therefore can self-express the same.

Meanwhile, the present inventors can mass-produce 2'-fucosyllactose, which is breast milk oligosaccharide, in *Corynebacterium glutamicum* (*C. glutamicum*) through the transformation strategy described above.

Meanwhile, according to the present invention, genes encoding α-1,2-fucosyltransferase are, for example, fucT2 genes, more preferably, fucT2 genes that have a nucleic acid sequence described in SEQ ID NO: 6, which is obtained by modifying a part of bases of wild-type fucT2 genes (for example, SEQ ID NO: 4). When fucT2 genes having a nucleic acid sequence described in SEQ ID NO: 6 are incorporated, the amount of produced 2'-fucosyllactose can be increased, compared to wild-type fucT2 genes.

Meanwhile, the present invention provides a method for producing 2'-fucosyllactose including culturing the recombinant *Corynebacterium glutamicum* of the present invention in a medium supplemented with lactose. When the recombinant *Corynebacterium glutamicum* strain according to the present invention is used, 2'-fucosyllactose can be produced at a high concentration, a high yield and a high productivity.

Meanwhile, regarding the method for producing 2'-fucosyllactose according to the present invention, the medium preferably further includes glucose. By adding glucose to the medium, growth of strain can be facilitated and 2'-fucosyllactose can thus be produced at a higher productivity.

Meanwhile, the method for producing 2'-fucosyllactose according to the present invention is preferably carried out by fed-batch culture that involves further supplying glucose or lactose. When glucose or lactose is continuously supplied by fed-batch culture, cell growth can be improved and fucosyllactose can be produced at a high purity, high yield and high productivity. The detailed technologies associated with fed-batch culture are well-known in the art and are not disclosed herein.

BRIEF DESCRIPTION OF THE DRAWINGS

The above and other objects, features and other advantages of the present invention will be more clearly understood from the following detailed description taken in conjunction with the accompanying drawings, in which:

FIG. 2 is a graph showing effects of incorporation of lacZ-removed lac operon (lacYA) on production of 2'-fucosyllactose in *Corynebacterium glutamicum* (*C. glutamicum*).

FIG. 3 is a graph showing results of batch culture using recombinant *Corynebacterium glutamicum* (*C. glutamicum*) pVBCL+pEGWT.

FIG. 4 shows results confirming production of 2'-fucosyllactose through LC-MS/MS analysis of a batch culture medium solution of recombinant *Corynebacterium glutamicum*.

FIG. 7 is a graph showing effects of incorporation of codon-optimized fucT2 genes (COfucT2) into *Corynebacterium glutamicum* (*C. glutamicum*) on production of 2'-fucosyllactose.

BEST MODE

Hereinafter, the present invention will be described in more detail with reference to the following examples, and the scope of the present invention is not limited to the examples and includes variations of technical concepts equivalent thereto.

Example 1: Production of Recombinant Strains and Plasmids

*Escherichia coli* TOP10 and *Corynebacterium glutamicum* (*C. glutamicum*) ATCC 13032 were used to produce plasmids and 2'-fucosyllactose (2'-FL), respectively.

In order to establish pVBCL plasmids, manB genes were amplified through PCR reaction using two DNA primers (F PstI-manB and R BamHI-SpeI-XbaI-manB) from the genomic DNAs of *Corynebacterium glutamicum* ATCC 13032, treated with restriction enzymes PstI and BamHI, and inserted into pVWEx2 plasmids which had been treated with the same restriction enzymes. manC genes were amplified again by PCR reaction using two DNA primers (F XbaI-manC and R SpeI-manC) from the genomic DNAs of *Corynebacterium glutamicum* ATCC 13032, treated with restriction enzymes XbaI and SpeI, and inserted into the established plasmid to establish pVmBC. In addition, lacYA gene clusters were amplified by PCR reaction using two DNA primers (F_inf_AsiSI_lacYA and R_inf_AsiSI_lacYA) from the pGlacYA plasmid established in the prior art (Korean Patent No. 10-1544184), treated with the restriction enzyme AsiSI and was inserted into the pVmBC plasmid which had been treated with the same restriction enzyme, to establish pVBCL plasmids.

In addition, in order to establish pEGWT plasmids, gmd-wcaG gene clusters were amplified by PCR reaction using two DNA primers (F_KpnI-gmd and R_SacI-wcaG) from the genomic DNAs of *Escherichia coli* K-12 MG1655, treated with restriction enzymes KpnI and SacI, and inserted into the pEKEx2 plasmid which had been treated with the same restriction enzymes to establish pEGW.

In addition, fucT2 genes were amplified by PCR reaction using two DNA primers (F_inf_SacI_RBS_fucT2 and R_inf_SacI_fucT2) from the genomic DNAs of *Helicobacter pylori* ATCC 700392, treated with the restriction enzyme SacI and inserted into the pEGW plasmid which had been treated with the same restriction enzyme to establish pEGWT.

Figure 1:
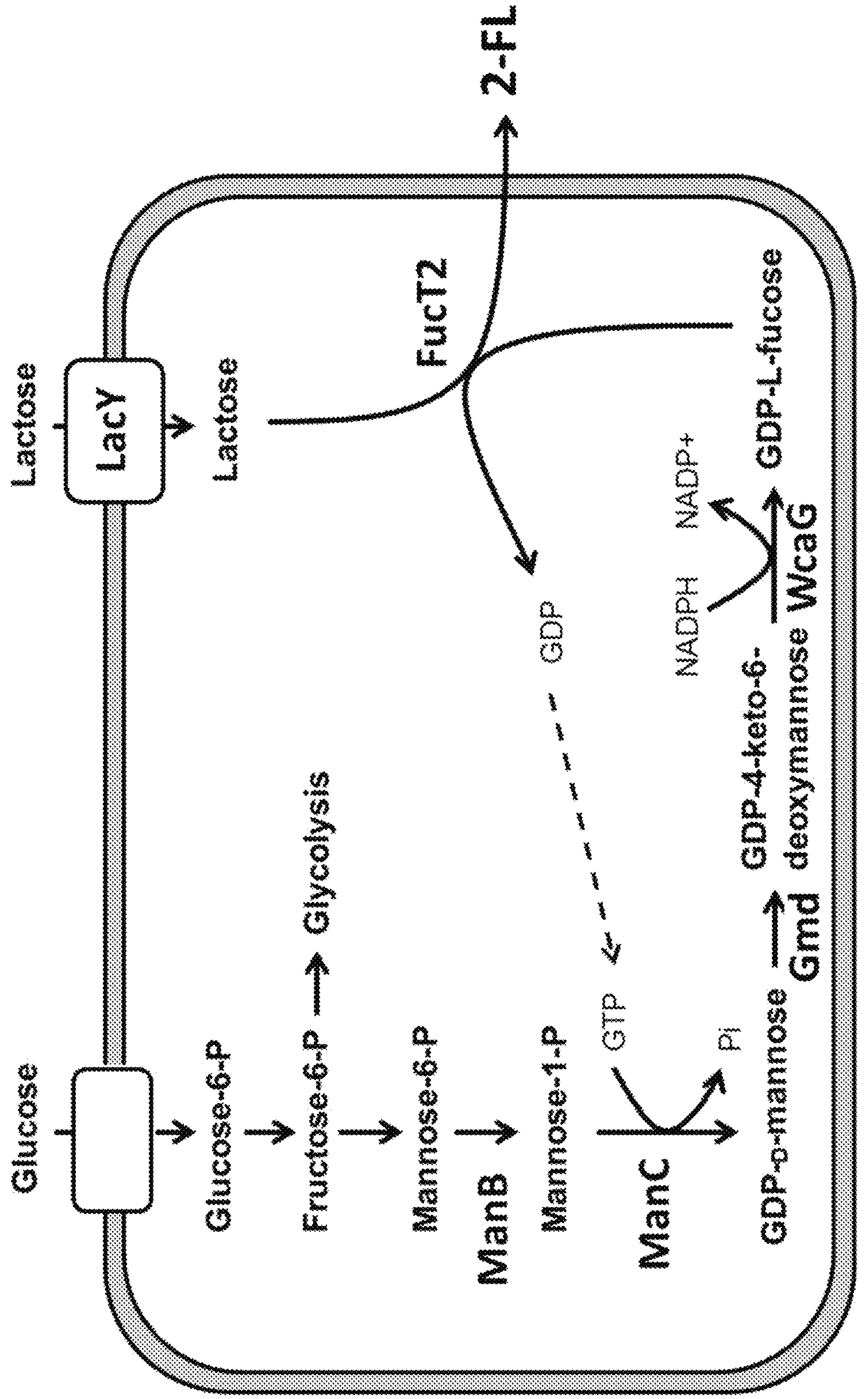
FIG. 1 shows a metabolic pathway to bio-synthesize GDP-L-fucose and fucosyllactose in *Corynebacterium glutamicum* (*C. glutamicum*) strain.
Figure 2A:
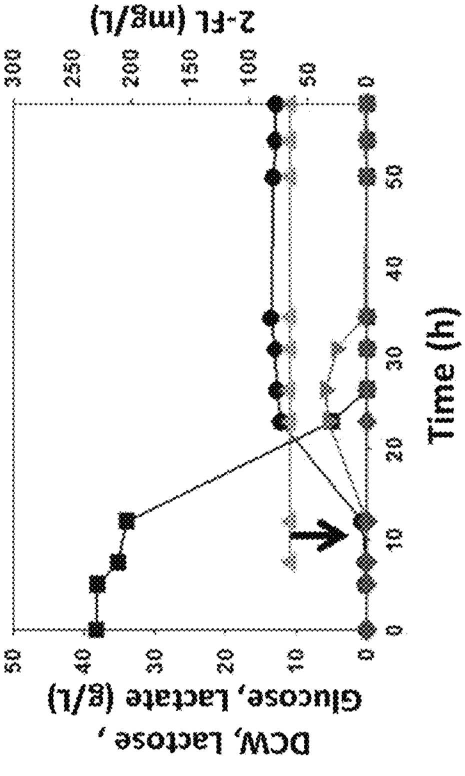
FIG. 2A shows results of culture of *Corynebacterium glutamicum* (*C. glutamicum*) strain that overexpress only ManB, ManC, Gmd and WcaG (Control Group)
Figure 2B:
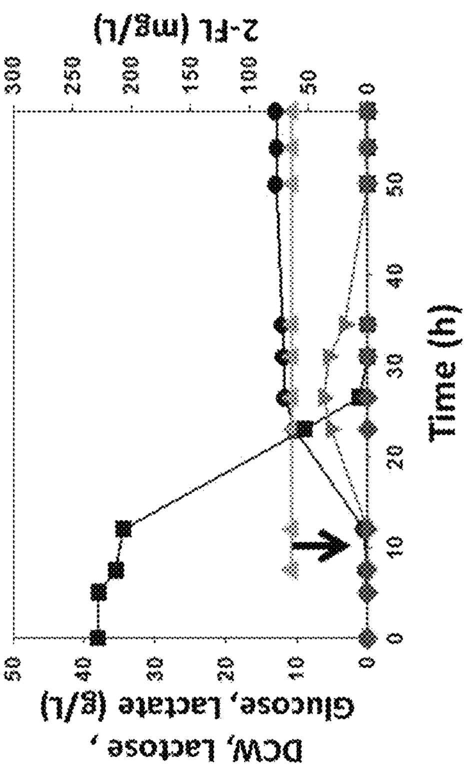
FIG. 2B shows culture results of the strain that overexpresses ManB, ManC, Gmd and WcaG, and allows for further incorporation of FucT2 (Comparative Example 1)
Figure 2C:
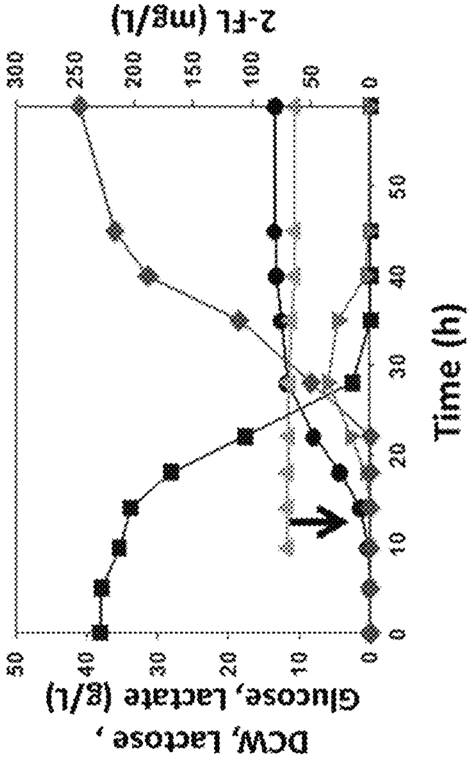
FIG. 2C shows culture results of the strain in which lac operon (lacYA), ManB, ManC, Gmd, WcaG, FucT2 and lacZ genes of which are removed, is incorporated (Example 1). Symbols in the graphs have the following meanings: ●: dried cell weight, ■: glucose, ▲: lactose, ▼: lactate, ♦: 2'-fucosyllactose.
Figure 2C:

In addition, codon-optimized fucT2 genes (COfucT2) were amplified by PCR reaction using two DNA primers (F_SacI_RBS_COfucT2 and R_SacI_COfucT2) designed from the pBHA (COfucT2) plasmid, and the amplified COfucT2 genes were treated with the restriction enzyme SacI and were inserted into the pEGW plasmid which had been treated with the same restriction enzyme, to establish pEGWT(CO) (FIG. 1). FIG. 1 shows a metabolic route to biosynthesize GDP-L-fucose and fucosyllactose in the *Corynebacterium glutamicum* strain.

The gene sequences, strains, plasmids and oligonucleotides used in the present Example are shown in the following Tables 1 to 4.

TABLE 1

Genes and gene sequences

| Names of genes | Sequence numbers |
|---|---|
| manB | SEQ ID NO: 1 |
| manC | SEQ ID NO: 2 |
| gmd-wcaG | SEQ ID NO: 3 |
| fucT2 | SEQ ID NO: 4 |
| lacYA | SEQ ID NO: 5 |
| COfucT2 | SEQ ID NO: 6 |

TABLE 2

Strains

| Strains | Related properties |
|---|---|
| *E. coli* TOP10 | $F^-$, mcrA Δ(mrr-hsdRMS-mcrBC) f801acZΔM15 lacX74 recA1 araD139Δ (ara-leu) 7697 galU galK rpsL ($Str^R$) endA1 nupG |
| *C. glutamicum* | Wild-type strain, ATCC 13032 |

TABLE 3

Plasmids

| Plasmids | Related properties |
|---|---|
| pEKEx2 | $Km^R$; *C. glutamicum/E. coli* shuttle vector for regulated gene expression ($P_{tac}$, lacIq, pBL1, oriVC.g., oriVE.c.) |
| pVWEx2 | $Tc^R$; *C. glutamicum/E. coli* shuttle vector for regulated gene expression ($P_{tac}$, lacIq, pHM1519, oriVC.g., oriVE.c.) |
| pGRG36 | Tn7 insertion vector, pSC101 replicon, $Amp^R$ |
| pBHA | Cloning vector, pUC replicon, $Amp^R$ |
| pGlacYA | pGRG36 + lacYA |
| pBHA(COfucT2) | pBHA + COfucT2 |
| pEGW | pEKEx2 + gmd-wcaG |
| pVmBC | pVWEx2 + manB + manC |
| pEGWT | pEGW + fucT2 |
| pVBCL | PVmBC + lacYA |
| pEGWT(CO) | pEGW + COfucT2 |

TABLE 4

| Primers | | |
|---|---|---|
| Primer names | Sequence (5'→3') | Sequence numbers |
| F_KpnI-gmd | GG**GGTACC***AAGGAGATATACA*ATGTCAAAAGTCGCTCTCATCACC | SEQ ID NO: 7 |
| R_SacI-wcaG | C**GAGCTC**TTACCCCCGAAAGCGGTCTTG | SEQ ID NO: 8 |
| F_PstI-manB | AA**CTGCAG***AAGGAGATATACA*ATGCGTACCCGTGAATCTGTCAC | SEQ ID NO: 9 |
| R_BamHI-SpeI-XbaI-manB | CG**GGATCC**GG**ACTAGT**GC**TCTAGA**TTATGCGCGGATAATCCCTA | SEQ ID NO: 10 |
| F_XbaI-manC | GC**TCTAGA***AAGGAGATATACA*ATGACTTTAACTGACAAC | SEQ ID NO: 11 |
| R_SpeI-manC | GG**ACTAGT**CTACTGATCAGACGAAAA | SEQ ID NO: 12 |
| F_inf_AsiSI_lacYA | GTCCTTTTAACA**GCGATCGC**ACCATCGAATGGCGCAAAACCTTTCG | SEQ ID NO: 13 |
| R_inf_AsiSI_lacYA | GAGACGAAATAC**GCGATCGC**GCTGTGGGTCAAAGAGGCATGATG | SEQ ID NO: 14 |
| F_inf_SacI_RBS_fucT2 | GGGGGTAACTTAAG**GAGCTC***AAGGAGATATACA*ATGGCTTTTAAGGTGGTGCAAATTTGCG | SEQ ID NO: 15 |
| R_inf_SacI_fucT2 | CGGCCAGTGAATTC**GAGCTC**TTAAGCGTTATACTTTTGGGATTTTACCTCAAAATG | SEQ ID NO: 16 |
| F_SacI_RBS_COfucT2 | C**GAGCTC***AAGGAGATATACA*ATGG | SEQ ID NO: 17 |
| R_SacI_COfucT2 | C**GAGCTC**TTATGCGTTATACTTCTG | SEQ ID NO: 18 |

* Sequences represented in italics mean RBSs (ribosome binding sites) and spacers.
* Sequences represented in bold type mean recognition sites of specific restriction enzymes

Example 2: Conditions and Methods for Culturing Recombinant *Corynebacterium glutamicum*

Seed culture was carried out using a test tube containing 5 mL of BHI (brain heart infusion) medium supplemented with an appropriate antibiotic (kanamycin 25 μg/mL, tetracycline 5 μg/mL) at a temperature of 30° C. and a constant stirring rate of 250 rpm for 12 hours.

Batch culture was carried out at 30° C. in a 500 mL bioreactor (Kobiotech, Incheon, Korea) containing 100 mL or 1 L of minimum medium (containing $(NH_4)_2SO_4$ 20 g/L, urea 5 g/L, $KH_2PO_4$ 1 g/L, $K_2HPO_4$ 1 g/L, $MgSO_4$ 0.25 g/L, MOPS 42 g/L, $CaCl_2$ 10 mg/L, Biotin 0.2 mg/L, protocatechuic acid 30 mg/L, $FeSO_47H_20$ 10 mg/L, $MnSO_4H_2O$ 10 mg/L, $ZnSO_47H_2O$ 1 mg/L, $CuSO_4$ 0.2 mg/L, $NiCl_26H_2O$ 0.02 mg/L, pH 7.0). The stirring rate during culture was maintained at 250 rpm for the flask and 1000 rpm and 2 vvm for the bioreactor. In case of batch culture, IPTG (isopropyl-β-D-thiogalactopyranoside) and lactose were added such that final concentrations were adjusted to 1.0 mM and 10 g/L, respectively, when optical density ($OD_{600}$) reached 0.8.

The fed-batch culture for high-concentration cell culture application was carried out in a 2.5 L bioreactor (Kobiotech, Incheon, Korea) containing 1.0 L of a minimum medium supplemented with 40 g/L of glucose and appropriate antibiotic (25 μg/mL of kanamycin, 5 μg/mL of tetracycline).

After the glucose added at an initial stage was completely consumed, a feeding solution including 800 g/L of glucose was supplied by a continuous feeding method at a rate of 5.7 g/L/h. At the same time, IPTG and lactose were added such that final concentrations were adjusted to 1.0 mM and 10 g/L, respectively in order to induce expression of tac promotor-mediated genes and thereby produce 2'-fucosyllactose.

When pH of the medium was lower than a set point during fermentation, 28% $NH_4OH$ was automatically supplied and when pH was higher than the set point, 2N HCl was added, so that pH could be maintained within a predetermined range of (pH 6.98 to 7.02). The pH of the medium was measured in real-time using a pH electrode (Mettler Toledo, USA). Stirring rate and aeration rate were maintained at 1,000 rpm and 2 vvm to prevent lack of oxygen.

Example 3: Determination of Concentrations of Cells and Metabolites

The dried cell weight was determined by multiplying the optical density (OD) by a pre-measured transmutation constant of 0.3. The optical density (OD) was adjusted to the range of 0.1 to 0.5 by diluting a sample at an appropriate level and absorbance at 600 nm was measured using a spectrophotometer (Ultrospec 2000, Amersham Pharmacia Biotech, USA).

The concentrations of 2'-fucosyllactose, lactose, lactate, glucose and acetic acid were measured using a high-performance liquid chromatography (HPLC) device (Agilent 1100LC, USA) equipped with a carbohydrate analysis column (Rezex ROA-organic acid, Phenomenex, USA) and a refractive index (RI) detector. 20 μl of the culture medium diluted (×10) was analyzed using a column pre-heated at 60° C. 5 mM of a $H_2SO_4$ solution was used as a mobile phase at a flow rate of 0.6 mL/min.

Test Example 1: Identification of Incorporation of lacZ Genes-Removed Lac Operon (lacYA) on Production of 2'-Fucosyllactose in *Corynebacterium glutamicum* (*C. glutamicum*)

In the present Test Example, in order to bio-synthesize 2'-fucosyllactose in *Corynebacterium glutamicum* (*C. glutamicum*), a lactose carrier was incorporated and effects thereof were identified.

For this purpose, lac operon (lacYA), *E. coli* K-12-derived lacZ genes of which are removed, established in the prior art (Korean Patent No. 10-1544184), was incorporated into *Corynebacterium glutamicum* to produce 2'-fucosyllactose.

In the prior art, in order to establish *Escherichia coli* that has no activity of β-galactosidase and has only activity of the lactose carrier, lac operon (lacYA) in which lac operon on the chromosome of *Escherichia coli* is removed and lacZ genes encoding β-galactosidase are removed is incorporated into the chromosome of *Escherichia coli* again, to produce 2'-fucosyllactose (Korean Patent No. 10-1544184).

Experimentation was conducted using the recombinant *Corynebacterium glutamicum* strain that overexpressed only ManB, ManC, Gmd, and WcaG, which are GDP-L-fucose biosynthesis enzymes (Control Group), the strain that overexpressed ManB, ManC, Gmd and WcaG, which are GDP-L-fucose biosynthesis enzymes, and to which FucT2 was further incorporated (Comparative Example 1), and the strain in which lac operon (lacYA) obtained by removing ManB, ManC, Gmd, WcaG, FucT2 and lacZ genes, which are GDP-L-fucose biosynthesis enzymes, was incorporated (Example 1). By comparing Control Group, Comparative Example 1 and Example 1 through batch culture in the flask, the effects of incorporation of lacYA operon and fucose transferase on production of 2'-fucosyllactose were evaluated.

As a result of experimentation, the *Corynebacterium glutamicum* strain that overexpressed only GDP-L-fucose-biosynthesis enzymes, ManB, ManC, Gmd and WcaG (Control Group), and the strain that overexpressed ManB, ManC, Gmd and WcaG, which are GDP-L-fucose biosynthesis enzymes, and in which FucT2 was further incorporated (Comparative Example 1), did not produce 2'-fucosyllactose at all.

However, only the strain in which lac operon (lacYA) obtained by removing ManB, ManC, Gmd, WcaG, FucT2 and lacZ genes, which are GDP-L-fucose biosynthesis enzymes, was incorporated (Example 1) produced 2'-fucosyllactose (Table 5 and FIG. 2). FIG. 2 is a graph showing effects of incorporation of lacZ-removed lac operon (lacYA) on production of 2'-fucosyllactose in *Corynebacterium glutamicum*. FIG. 2A shows culture results of Control Group, FIG. 2B shows culture results of Comparative Example 1 and FIG. 2C shows culture results of Test Example 1.

The results indicate that, as a lactose carrier is incorporated, lactose is incorporated into the strain and is used to produce 2'-fucosyllactose, which means that incorporation of lacZ genes-removed lac operon (lacYA) is essential for the production of 2'-fucosyllactose.

TABLE 5

Identification of effects of incorporation of lacZ-removed lac operon (lacYA) on production of 2'-fucosyllactose in *Corynebacterimn glutamicum* (*C. glutamicum*)

| Plasmid | Final dried cell weight (g/L) | Lactose consumption[a] (g/L) | Maximum 2'-fucosyllactose concentration[a] (mg/L) | Yield (moles of 2'-fucosyllactose/moles of lactose) | Productivity[a] (mg/L/h) |
|---|---|---|---|---|---|
| pVBC pEGW | 13.5 | 0.02 | N.D. | — | — |
| pVBC pEGWT | 12.9 | 0.02 | N.D. | — | — |
| pVBCL pEGWT | 13.4 | 0.78 | 246 | 0.22 | 5.0 |

Test Example 2: Production of 2'-fucosyllactose Through Batch Culture

In order to find the capability of the recombinant *Corynebacterium glutamicum* (*C. glutamicum*) established in Test Example 1, to produce 2'-fucosyllactose and fermentation features thereof, recombinant *Corynebacterium glutamicum*, in which lac operon (lacYA) from which ManB, ManC, Gmd, WcaG, FucT2 and lacZ were removed was incorporated was batch-cultured in a flask and a fermenter. IPTG and lactose were added such that final concentrations were adjusted to 1.0 mM and 10 g/L, respectively, when the optical density ($OD_{600}$) reached 0.8.

As a result of flask batch culture, 246 mg/L of 2'-fucosyllactose was produced. The yield (ratio of moles of 2'-fucosyllactose to moles of lactose) was 0.22 mole/mole, and productivity was 4.97 mg/L/h (FIG. 3 and Table 6).

Meanwhile, in case of fermenter batch culture, 274 mg/L of 2'-fucosyllactose was produced, the yield (ratio of moles of 2'-fucosyllactose to moles of lactose) was 0.34 mole/mole and productivity was 5.6 mg/L/h. Compared to the flask culture, the final concentration, yield and productivity of 2'-fucosyllactose were increased by about 11%, 55% and 12%, respectively. This is due to the fact that the fermenter could efficiently control conditions such as temperature, pH and oxygen supply compared to the flask culture.

Figure 3B:
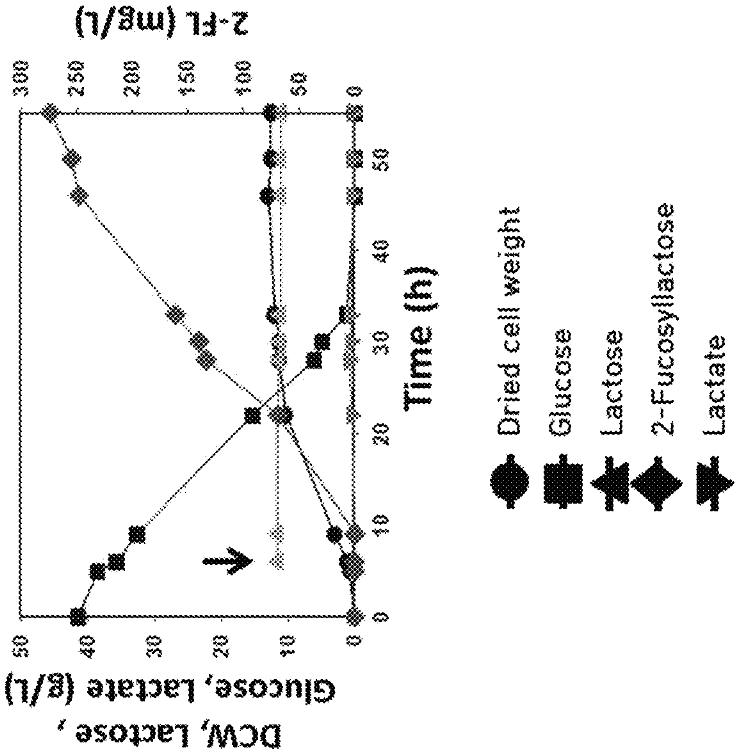
FIG. 3A shows results of flask batch culture and FIG. 3B shows results of fermenter batch culture. When optical density ($OD_{600}$) reaches about 0.8, IPTG and lactose are added to allow final concentrations to become 1.0 mM, and 10 g/L (arrows). Symbols in the graphs have the following meanings: ●: Dried cell weight, ■: Glucose, ▲: Lactose, ▼: Lactate, ♦: 2'-Fucosyllactose.
Figure 3A:
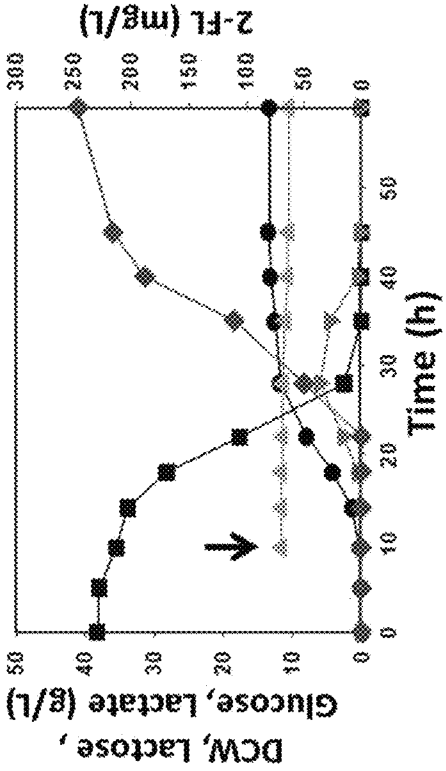

Results of the batch culture are shown in the following Table 6, FIG. 3 is a graph showing results of batch culture using recombinant *Corynebacterium glutamicum* (*C. glutamicum*) pVBCL+pEGWT, FIG. 3A shows results of flask batch culture and FIG. 3B shows results of fermenter batch culture.

TABLE 6

Results of batch culture using recombinant *Corynebacterium glutamicum* (*C. glutamicum*) pVBCL + pEGWT

| | Final dried cell weight (g/L) | Lactose consumption[a] (g/L) | Maximum 2'-fucosyllactose concentration[a] (mg/L) | Yield (moles of 2'-fucosyllactose/moles of lactose) | Productivity[a] (mg/L/h) |
|---|---|---|---|---|---|
| Flask | 13.4 | 0.78 | 246 | 0.22 | 4.97 |
| Fermenter | 13.0 | 0.57 | 274 | 0.34 | 5.6 |

[a]Concentrations of lactose and 2'-fucosyllactose are calculated from only lactose and 2'-fucosyllactose present in medium.

Test Example 3: Identification of Production of 2'-Fucosyllactose Through LC-MS/MS Analysis Qualitative analysis was conducted by LC-MS/MS in order to identify 2'-fucosyllactose produced by batch culture of Test Example 2.

As a result of measurement of molecular weight in a cation mode using MALDI-TOP MS, the peak of 511.164 m/z, which corresponds to the molecular weight of 2-fucosyllactose having one sodium molecule bonded thereto was observed.

Figure 4A:
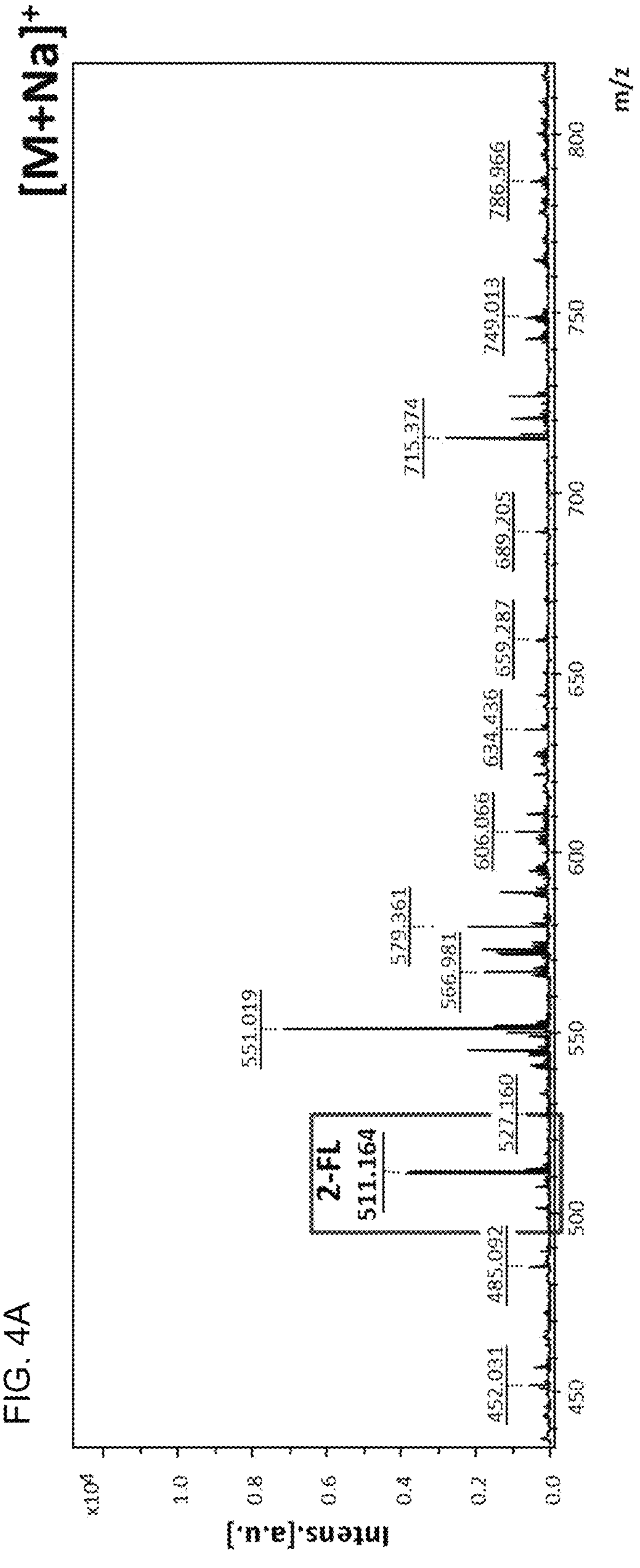
FIG. 4A is a graph showing production of fucosyllactose through molecular weight analysis in a cation mode using MALDI-TOP MS and FIG. 4B is a graph showing structural composition of fucosyllactose identified by tandem mass spectrometry (MS/MS)
Figure 4B:
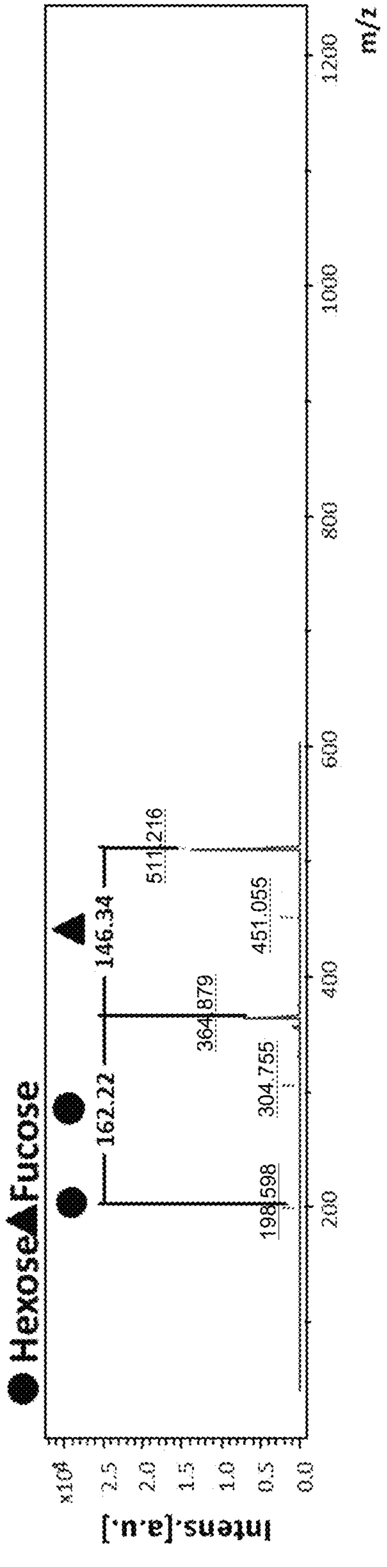

In addition, as a result of tandem mass spectrometry (MS/MS) analysis to identify the structural composition of the peak, glucose, galactose and fucose that constitute 2'-fucosyllactose were found (FIG. 4). FIG. 4 shows results identifying production of 2'-fucosyllactose through LC-MS/MS analysis of the culture solution of recombinant *Corynebacterium glutamicum*. FIG. 4A shows results identifying production of fucosyllactose through molecular weight analysis of ingredients contained in the culture solution in a cation mode using MALDI-TOP MS, and FIG. 4B shows tandem mass spectrometry (MS/MS) results structurally identifying the fact that the peak of 511.134 m/z corresponds to 2'-fucosyllactose.

As a result of experimentation, 2'-fucosyllactose was produced in the batch culture.

Test Example 4: Production of 2'-fucosyllactose Through Fed-Batch Culture

In order to produce high-concentration 2'-fucosyllactose through high-concentration cell culture, fed-batch culture was conducted in a 2.5 L fermenter using recombinant *Corynebacterium glutamicum* (*C. glutamicum*) in which pVBCL and pEGWT plasmids were incorporated.

When 40 g/L glucose supplied at an initial stage was completely consumed, a feeding solution started to be supplied at a rate of 5.7 g/L/h by a continuous feeding method in order to maintain cell growth. At the same time, IPTG and lactose were added to induce production of 2'-fucosyllactose.

As a result of experimentation, acetic acid was not produced at all during fermentation, and the cells had a dried cell weight of 57.3 g/L through metabolism of glucose. In addition, maximum concentration of 2'-fucosyllactose was 5.8 g/L, the yield (ratio of moles of 2'-fucosyllactose to moles of lactose) was 0.55 mole/mole and productivity was 0.06 g/L/h (FIG. 5 and Table 7).

Figure 5:
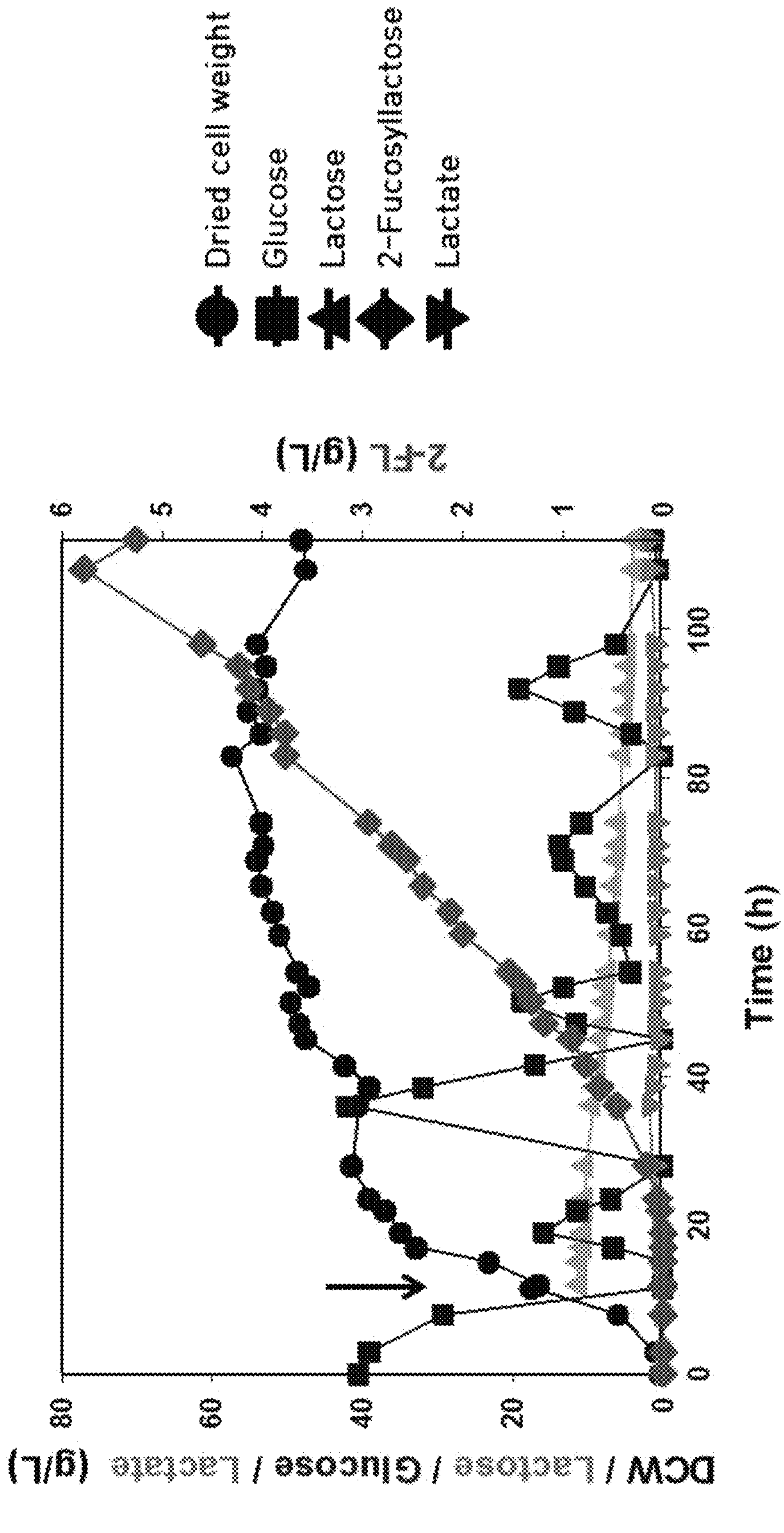
FIG. 5 is a graph showing results of fed-batch culture using recombinant *Corynebacterium glutamicum* (*C. glutamicum*) pVBCL+pEGWT. After 40 g/L glucose supplied at an initial stage was completely consumed, glucose started to be supplied by a continuous feeding method. At the same time, IPTG and lactose were added (large arrows). Symbols in the graphs have the following meanings: ●: Dried cell weight, ■: Glucose, ▲: Lactose, ▼: Lactate, ♦: 2'-Fucosyllactose.

Results of fed-batch culture to produce 2'-fucosyllactose are shown in the following Table 7, and FIG. 5 is a graph showing results of fed-batch culture using recombinant *Corynebacterium glutamicum* pVBCL+pEGWT.

TABLE 7

Results of fed-batch culture using recombinant *Corynebacterium glutamicum* (*C. glutamicum*) pVBCL + pEGWT

| Plasmid | Final dried cell weight (g/L) | Lactose consumption[a] (g/L) | Maximum 2'-fucosyllactose concentration[a] (g/L) | Yield (moles of 2'-fucosyllactose/ moles of lactose) | Productivity[a] (g/L/h) |
|---|---|---|---|---|---|
| pVBCL pEGWT | 57.3 | 7.3 | 5.8 | 0.55 | 0.06 |

[a]2-FL productivity was calculated after IPTG induction.

[b]Concentrations of lactose and 2'-fucosyllactose are calculated from only lactose and 2'-fucosyllactose present in medium.

[Test Example 5: Effects of Incorporation of Codon-Optimized fucT2 Genes (COfucT2) on Production of 2'-Fucosyllactose by Recombinant *Corynebacterium glutamicum* (*C. glutamicum*)]

(1) Production of Codon-Optimized fucT2 Genes (COfucT2)

In order to improve translation efficiency of fucT2 genes which are *Helicobacter pylori* (*H. pylori*)-derived α-1,2-fucosetransferase in recombinant *Corynebacterium glutamicum* (*C. glutamicum*), the fucT2 genes were codon-optimized depending on codon usage of *Corynebacterium glutamicum.*

Figure 6:
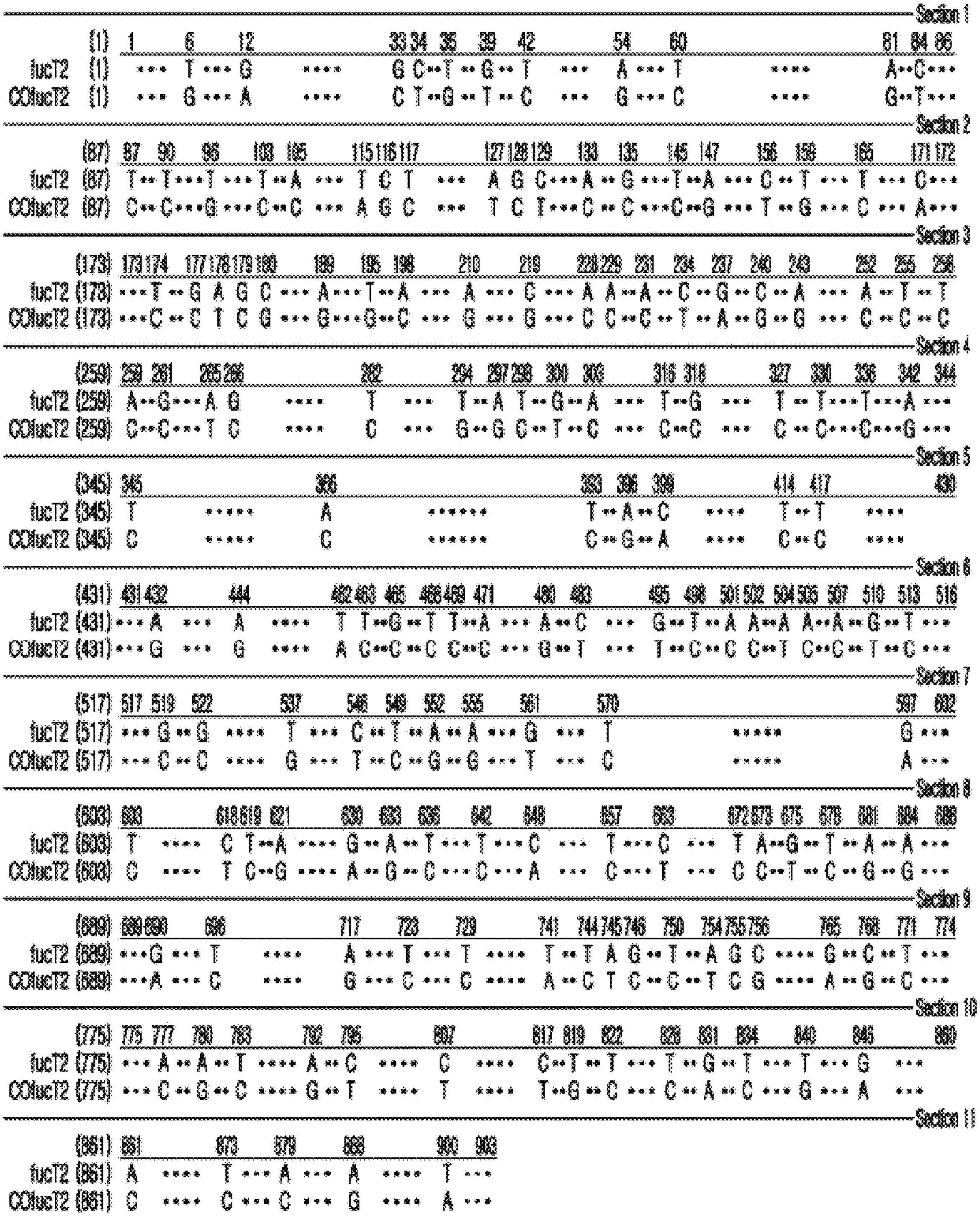
FIG. 6 shows results of codon-optimization of fucT2 genes to be suited to *Corynebacterium glutamicum* (*C. glutamicum*) in order to improve translation efficiency of fucT2 genes.

As a result of experimentation, when compared with conventional fucT2 genes, about 17.1% of the sequence was mutated (FIG. 6). FIG. 6 shows results of codon-optimization of fucT2 genes to be suited to *Corynebacterium glutamicum* (*C. glutamicum*).

(2) Identification of Effects of Incorporation of Codon-Optimized fucT2 Genes (COfucT2) on Production of 2'-Fucosyllactose In order to find the capability of the recombinant *Corynebacterium glutamicum* (*C. glutamicum*) established using codon-optimized fucT2 genes (COfucT2) to produce 2'-fucosyllactose, and fermentation features thereof, batch culture and fed-batch culture were carried out in a flask and a fermenter, respectively.

In case of batch culture, IPTG and lactose were added such that final concentrations were adjusted to 1.0 mM and 10 g/L, respectively, when the optical density ($OD_{600}$) reached 0.8. In case of fed-batch culture, when 40 g/L glucose supplied at an initial stage was completely consumed, a feeding solution started to be supplied at a rate of 5.7 g/L/h by a continuous feeding method to maintain cell growth. At the same time, IPTG and lactose were added to induce production of 2'-fucosyllactose.

Figure 7B:
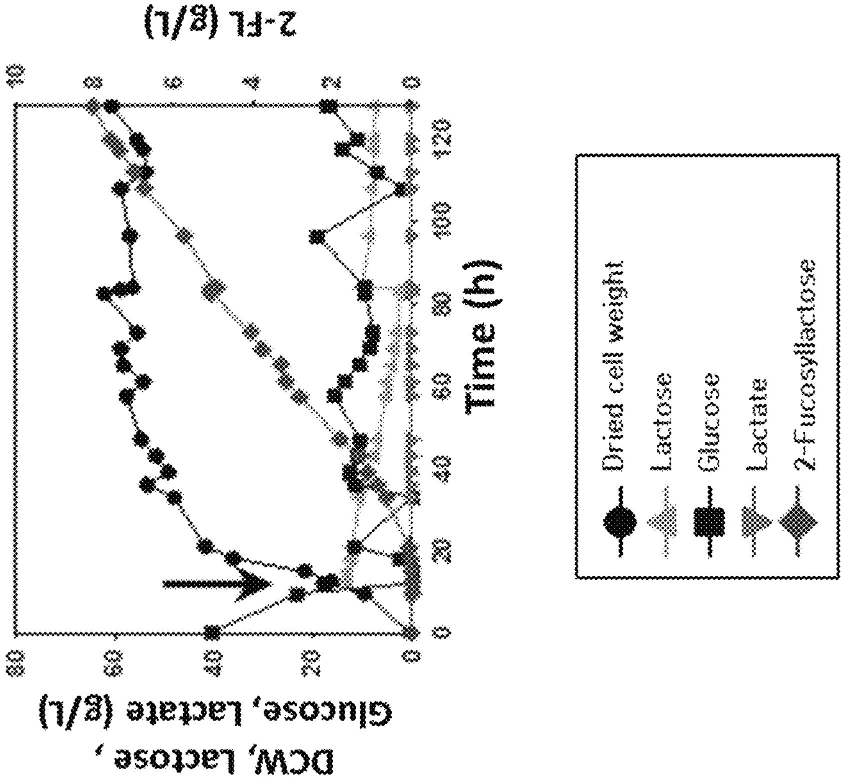
FIG. 7B is a graph showing results of fermenter fed-batch culture using recombinant *Corynebacterium glutamicum* (*C. glutamicum*) pVBCL+pEGWT (CO). After 40 g/L glucose supplied at an initial stage was completely consumed, glucose started to be supplied by a continuous feeding method. At the same time, IPTG and lactose were added (large arrows). Symbols in the graphs have the following meanings: ●: Dried cell weight, ■: Glucose, ▲: Lactose, ▼: Lactate, ♦: 2'-Fucosyllactose.
Figure 7A:
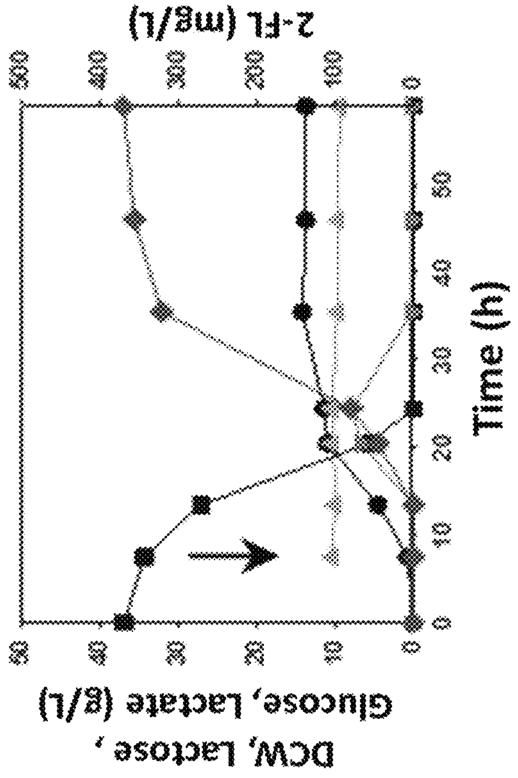
FIG. 7A is a graph showing results of flask batch culture using recombinant *Corynebacterium glutamicum* (*C. glutamicum*) pVBCL+pEGWT (CO). When optical density ($OD_{600}$) reached about 0.8, IPTG and lactose were added to allow final concentrations to become 1.0 mM, and 10 g/L (arrows).

As a result of batch culture, 370 mg/L of 2'-fucosyllactose was produced, the yield (ratio of moles of 2'-fucosyllactose to moles of lactose) was 0.28 mole/mole and productivity was 7.18 mg/L/h (FIG. 7A and Table 8). Compared to results of Test Example 2, the final concentration, yield and productivity of 2'-fucosyllactose were increased by about 50%, 27% and 44%, respectively.

Meanwhile, as a result of fed-batch culture, 8.1 g/L of 2'-fucosyllactose was produced, the yield (ratio of moles of 2'-fucosyllactose to moles of lactose) was 0.42 mole/mole and productivity was 0.07 g/L/h (FIG. 7B and Table 8). Compared to results when wild-type fucT2 was incorporated (Test Example 4), the final concentration and productivity of 2'-fucosyllactose were increased by about 39% and 17%, respectively.

The results of culture are shown in the following Table 8, FIG. 7A is a graph showing results of flask batch culture using recombinant *Corynebacterium glutamicum* (*C. glutamicum*) pVBCL+pEGWT (CO), and FIG. 7B is a graph showing results of fermenter fed-batch culture using recombinant *Corynebacterium glutamicum* (*C. glutamicum*) pVBCL+pEGWT(CO).

TABLE 8

Results of batch and fed-batch culture using recombinant *Corynebacterium glutamicum* (*C. glutamicum*) pVBCL + pEGWT(CO)

| | Final dried cell weight (g/L) | Lactose consumption[a] (g/L) | Maximum 2'-fucosyllactose concentration[a] | Yield (moles of 2'-fucosyllactose/moles of lactose) | Productivity[a] |
|---|---|---|---|---|---|
| Batch (flask) | 14.2 | 0.94 | 370 (mg/L) | 0.28 | 7.18 (mg/L/h) |
| Fed-batch (fermenter) | 62.1 | 13.6 | 8.1 (g/L) | 0.42 | 0.07 (g/L/h) |

[a]2-FL productivity was calculated after IPTG induction.

[b]Concentrations of lactose and 2'-fucosyllactose were calculated from only lactose and 2'-fucosyllactose present in medium.

The invention claimed is:

1. A method of producing 2'-fucosyllactose comprising culturing in a medium supplemented with lactose a recombinant *Corynebacterium glutamicum* transformed to express α-1,2-fucosyltransferase, transformed to express GDP-Dmannose-4,6-dehydratase, transformed to express GDP-L-fucose synthase, and transformed to express lactose permease, and isolating 2'-fucosyllactose from the medium, wherein the recombinant *Corynebacterium glutamicum* has phosphomannomutase and GTP-mannose-1-phosphate guanylyltransferase.

2. The method according to claim 1, wherein the medium further comprises glucose.

3. The method according to claim 2, wherein the production of the fucosyllactose is carried out by fed-batch culture comprising further supplying glucose or lactose.

4. The method according to claim 1, wherein the recombinant *Corynebacterium glutamicum* is transformed to overexpress phosphomannomutase, and transformed to overexpress GTP-mannose-1-phosphate guanylyltransferase.

* * * * *